United States Patent
Beard et al.

(10) Patent No.: US 7,809,513 B2
(45) Date of Patent: ***Oct. 5, 2010

(54) ENVIRONMENTAL CHANGE COMPENSATION IN A STRUCTURAL HEALTH MONITORING SYSTEM

(75) Inventors: Shawn J. Beard, Livermore, CA (US); Bao Liu, Cupertino, CA (US); Fu-Kuo Chang, Stanford, CA (US)

(73) Assignee: Acellent Technologies, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/952,936

(22) Filed: Dec. 7, 2007

(65) Prior Publication Data

US 2008/0255775 A1 Oct. 16, 2008

Related U.S. Application Data

(60) Provisional application No. 60/912,112, filed on Apr. 16, 2007.

(51) Int. Cl.
| | |
|---|---|
| *G01N 17/00* | (2006.01) |
| *G01N 25/00* | (2006.01) |
| *G01M 19/00* | (2006.01) |
| *G01D 21/00* | (2006.01) |
| *G01H 17/00* | (2006.01) |
| *G06F 19/00* | (2006.01) |
| *G06F 17/40* | (2006.01) |

(52) U.S. Cl. ................... 702/34; 73/865.8; 374/57; 378/58; 702/187; 702/189

(58) Field of Classification Search ............. 702/105, 702/1, 33, 34, 35, 41, 42, 85, 104, 108, 113, 702/116, 127, 130, 136, 138, 182, 187, 188, 702/189; 73/760, 786, 865.8, 865.9, 866; 374/45, 57; 378/1, 51, 58; 382/100, 141; 700/90, 95, 108, 109, 110
See application file for complete search history.

(56) References Cited

U.S. PATENT DOCUMENTS

| | | | | |
|---|---|---|---|---|
| 3,517,177 | A * | 6/1970 | Crowell | 702/34 |
| 6,055,480 | A * | 4/2000 | Nevo et al. | 702/3 |
| 7,366,627 | B2 * | 4/2008 | Gordon et al. | 702/105 |
| 7,635,338 | B2 * | 12/2009 | Eide | 600/485 |
| 2003/0100845 | A1 * | 5/2003 | Eide | 600/561 |
| 2006/0047201 | A1 * | 3/2006 | Eide | 600/485 |
| 2008/0255771 | A1 * | 10/2008 | Beard | 702/34 |
| 2008/0255774 | A1 * | 10/2008 | Liu et al. | 702/34 |
| 2009/0062625 | A1 * | 3/2009 | Eide | 600/300 |
| 2009/0062688 | A1 * | 3/2009 | Eide | 600/561 |
| 2009/0062689 | A1 * | 3/2009 | Eide | 600/561 |

(Continued)

*Primary Examiner*—Edward R Cosimano
(74) *Attorney, Agent, or Firm*—Innovation Counsel LLP

(57) ABSTRACT

A method and system of compensating for environmental effect when detecting signals using a structural health monitoring system includes collecting baseline data signals for one or more values of the environmental effect variable from signals transmitted along selected paths between transducers in an array attached to the structure. A threshold is selected based on the baseline data for determining if the signal is detected. Current data signals are collected and matched to the best fit baseline data. The value of the environmental effect variable is determined on the basis of the matching. A signal is detected according to the selected threshold.

20 Claims, 5 Drawing Sheets

U.S. PATENT DOCUMENTS

| | | | |
|---|---|---|---|
| 2009/0069700 A1* | 3/2009 | Eide | 600/485 |
| 2009/0069710 A1* | 3/2009 | Eide | 600/561 |
| 2009/0069711 A1* | 3/2009 | Eide | 600/561 |
| 2009/0124910 A1* | 5/2009 | Eide | 600/485 |

* cited by examiner

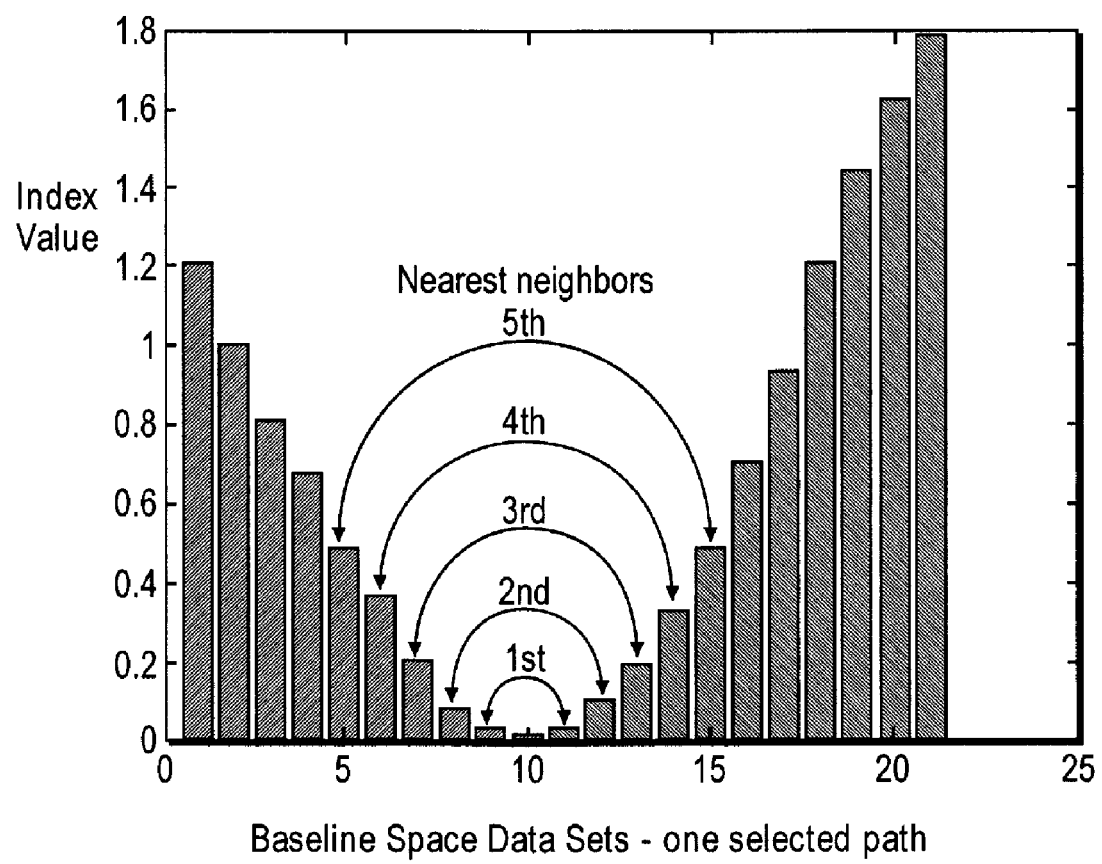

ENVIRONMENTAL CHANGE COMPENSATION IN A STRUCTURAL HEALTH MONITORING SYSTEM

This application claims the benefit of U.S. Provisional Patent Application Ser. No. 60/912,112 now expired, entitled "STRUCTURAL HEALTH MONITORING SYSTEM AND METHODS FOR USE," filed on Apr. 16, 2007, which is hereby incorporated by reference in its entirety.

BRIEF DESCRIPTION OF THE INVENTION

This invention relates generally to structural health monitoring. More specifically, this invention relates to methods of compensating for effects of environmental changes.

BACKGROUND OF THE INVENTION

Current state-of-the-art methodologies in structural damage detection rely heavily on the use of baseline data collected from the structure in the undamaged state. The methodologies are based on excitation and detection of elastic waves between transducer actuators and sensors, comparing the current sensor responses to previously recorded baseline sensor responses, and using the differences to glean information about structural damage. It is known that environmental effects (such as temperature) will cause changes in the recorded signals, including baseline data, which in turn will interfere with most damage detection schemes. Therefore, to overcome this difficulty it is desirable to have a method to compensate for effects such as temperature to assure more accurate structural health monitoring.

SUMMARY OF THE INVENTION

Techniques are disclosed utilizing multiple sets of data to compensate for effects caused by environmental changes that may alter the response of an array of transducers in structural health monitoring systems. The data sets may be obtained from the structure's array under various environmental conditions. For example, data may be collected from the structure at different temperatures and/or at different times. Other environmental variables used may include load, strain, moisture content, any environmental condition that may cause a change in the response of a transducer, which is typically calibrated for a given set of conditions. The data sets obtained for each incremental value of the environmental parameter may be used to dynamically create a baseline for each individual actuator-sensor path of the array and corresponding region of the structure. At a later time, when an array scan is performed to search for damage, the newly recorded signals are compared to the dynamically created baseline, and the effects of the environmental variable offset.

The method may also be used to determine a "best fit" function curve to the variable, and provide a continuous correction for all values in the variable range. Thus, reading and correcting signals transmitted between transducers along corresponding transmit-receive paths and regions of the structure, using the baseline data as a basis for correction, may provide a more accurate method of damage assessment.

In one embodiment of the disclosure, a method of compensating data for environmental effect changes when detecting a signal includes collecting baseline data signals for one or more values of the environmental effect variable. A threshold is selected based on the baseline data for determining if the signal is detected. Current data signals are collected and matched to the best fit baseline data. The value of the environmental effect variable is determined on the basis of the matched data. A signal is detected in the collected data according to the selected threshold.

In an embodiment of the disclosure a method for collecting baseline data signals includes selecting one or more paths between a plurality of transducers arranged in an array on a structure. A range and set of values of the environmental effect variable are selected. A data signal transmitted on a first selected path between two transducers for a first value of the environmental effect variable is collected. The collecting is repeated for all selected paths, and for all values of the environmental effect variable.

A system for compensating for environmental effect changes in data in a structural health monitoring system operably coupled to a structure includes one or more transducers configured in an array and one or more environmental sensors to measure values of an environmental effect variable attached to the structure. A first software module acquires and processes data from the array to provide a baseline date set for calibrating the signals according to the values of the environmental effect variable and selecting a detection threshold. A second software module acquires and processes structural health monitoring current data from the array to detect damage in the structure by compensating the data for changes in the environmental effect variable. A memory stores the first and second software modules, acquires calibration data, structural health monitoring current data and data processed on the basis of the acquired calibration and monitoring data. A processor executes the instructions of the first and second software module. An interface operably couples the processor and memory to the array, and a display is operably coupled to the processor for presentation of damage located in the structure.

These and other features and advantages of the present invention will be more readily apparent from the detailed description of the preferred embodiments set forth below taken in conjunction with the accompanying drawings.

BRIEF DESCRIPTION OF THE FIGURES

FIG. 5 shows an exemplary graph of index values for a given actuator-sensor path according to an embodiment of the present disclosure.

Like element numbers in different figures represent the same or similar elements.

DETAILED DESCRIPTION

Methods and systems are disclosed for compensating data acquired in a structural health monitoring system for environmental effects.

Figure 1:
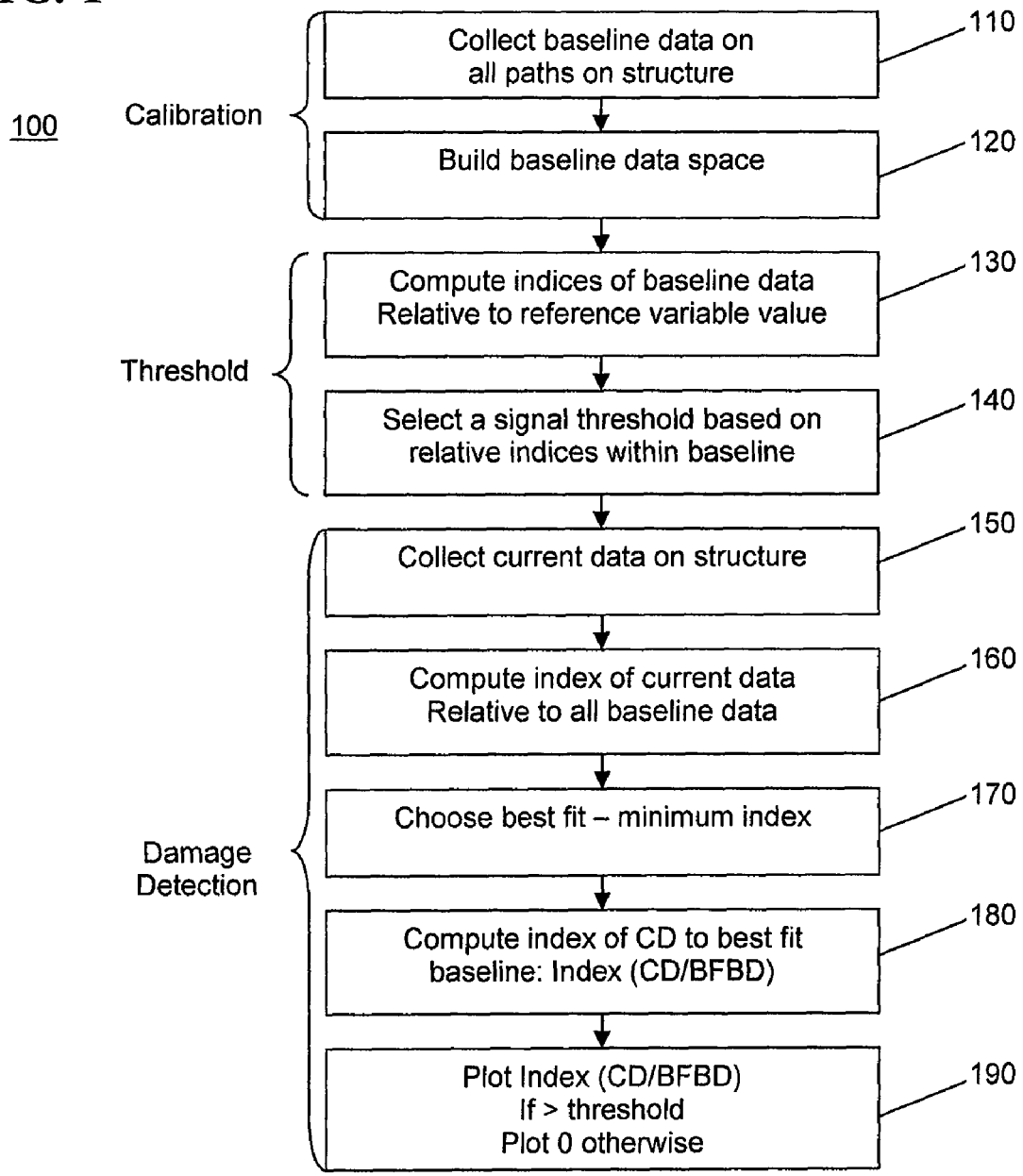
FIG. 1 is a flow chart of a method of compensating data for environmental effect changes when detecting a signal according to an embodiment of the present disclosure.

FIG. 1 is a flow chart of a method 100 of compensating data for environmental effect changes when detecting a signal according to an embodiment of the present disclosure.

Method 100 includes collecting baseline signal data (block 110) pertaining to a structure. For example, the signal data may be elastic waves excited by one or more transducers configured in an array attached to the structure as part of a structural health monitoring system. Elastic waves may be detected along paths selected between transducers in the array. The signal data may be collected for a plurality of values of an environmental effect variable, such as temperature, and the signal data and corresponding variable value may be stored (block 120) in a baseline data space to establish a baseline set of data for all paths and variable values, which will be described in more detail below.

The baseline data space may be used to establish an index (block 130) for each baseline data signal relative to a reference baseline data signal. This data space becomes the basis for establishing a threshold level (block 140) for determining if a signal is detected corresponding to damage in the structure.

Current signal data is collected (block 150) through the structural health monitoring system for each of the selected paths between transducers in the array. The current signal data of the selected path is compared to the baseline data by computing a current data index (block 160) relative to all baseline signal data for the corresponding environmental effect variable values. A best fit between the current signal data and a particular baseline signal data is found (block 170) on the basis of the minimum value of the current data index computed relative to all baseline signal data, i.e., a current data best fit index value for the selected path. The temperature of the structure along the selected path may be inferred from the best fit baseline signal data found to best match the current data.

The minimum value of the index of the current signal data is compared to the index of the best fit baseline data (block 180) which was used to establish calibration for changes due to the environmental effect. The index corresponding to the threshold level (determined in block 140) may be subtracted from the minimum value of the current data best fit index, i.e., the current data best fit index value (determined in block 170), where the subtraction is performed in block 190. If the result of the difference value is a positive number, a signal corresponding to damage is determined, and the current data index represents a measure of the damage signal. If the result of the difference value is equal to or less than zero, no signal is determined to exceed the threshold and a value of zero may be assigned as a measure of the damage signal. A representation of the difference values may be presented (block 190), for example, as a plot of the assigned measure of either the current data best fit index or zero. The plot may be, for example, a color coded plot according to the assigned measure, a topograph, or a table of assigned values. The representation has thus been compensated for environmental effects by plotting information obtained from best fit baseline data.

Figure 2:
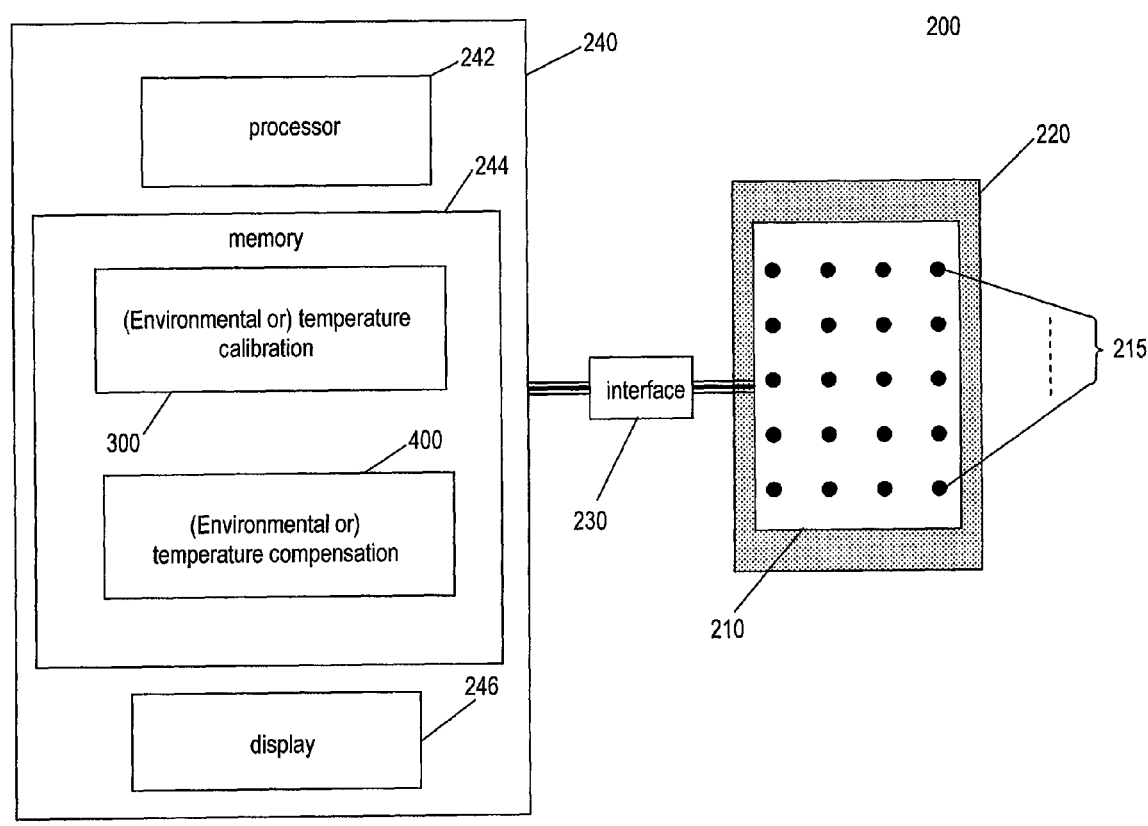
FIG. 2 is a system for compensating data in a structural health monitoring system due to environmental change, according to an embodiment of the disclosure.

FIG. 2 is a system 200 for compensating data in a structural health monitoring system due to environmental change, according to an embodiment of the disclosure. For the sake of simplicity, the embodiment will be described with respect to temperature as the environmental variable. However, other variables may be considered, such as load, strain, moisture content, humidity, pH or any other environmental variable that may causes changes in the behavior of the transducers, structure and corresponding signals.

System 200 includes an array 210 of transducers 215 attached to a structure 220 to be monitored for damage. Array 210 is operably coupled to an interface 230 for communication of signals and data between array 210 and a computer 240. Computer 240 comprises a processor 242 and a memory 244. Processor 242 is configured to execute instructions from software modules temperature calibration method 300 (described below) and temperature compensated detection method 400 (described below), both of which may be stored in memory 244. In addition, memory 244 may receive and store data comprising various data sets (not shown) as described above. Computer 240 may further comprise a display 246 or other output means (not shown) for presentation of damage detection information at various stages of compensation. Display 246 may, for example, be a computer monitor, a printer, or any means operably coupled to computer 240 for presentation of information.

Figure 3:
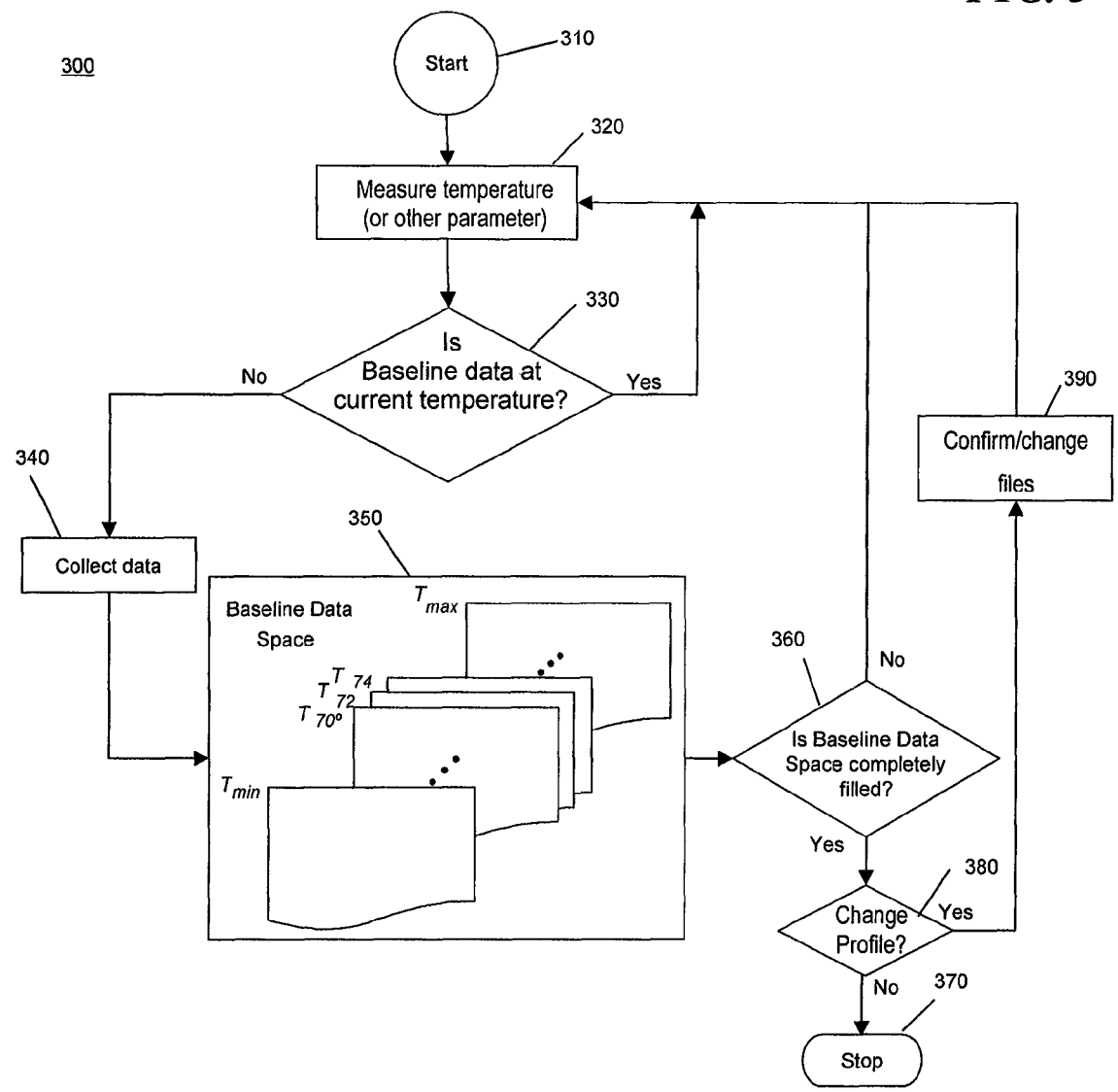
FIG. 3 is a flow chart of a method to calibrate baseline data according to an embodiment of the present disclosure.

FIG. 3 shows an embodiment of a calibration method 300 for establishing a baseline set of data of the performance of a transducer array attached to a structure as part of a structural health monitoring system.

One or more temperature sensors (not shown) may be attached to structure 220, preferably in proximity to transducers 215 of array 210 or selected paths between transducers 215. Equivalently, stress, strain or moisture sensors may be used. The transducers 215 may be, for example, piezoelectric, magneto-elastic, electrostatic or any other suitable elements adapted, when attached to structure 220, to excite and/or detect elastic waves in the body or on the surface of structure 220. In the embodiment being described herein, it is assumed that the structure initially has no detectable damage. Once started (block 310), calibration method 300 proceeds to acquire temperature readings (block 320) at selected locations on structure 220.

Hereinafter, it may be assumed that array 210 and structure 220 are at substantially the same temperature at least at each respective location of the one or more temperature sensors. However, this is not a requirement, and the temperature at each of the selected paths may be different, provided they can be measured. In Start block 310, temperature measurements may be user defined, e.g., they may be made at selected values, or may be made at temperatures of one or more specified increments over a range from a minimum temperature $T_{min}$ to a maximum temperature $T_{max}$. These parameters for acquiring calibration data may be selected, for example, via a graphical user interface provided by a temperature calibration control program. For example, as indicated above, the user may enter $T_{min}$, $T_{max}$, and temperature increments $\Delta T$, and a stabilization dwell time $\Delta t$, i.e., a delay time between setting temperature and when the measurement is made to provide a temperature stable measurement of signals. $\Delta T$ may be a fixed or unevenly spaced temperature interval. Alternatively, for example, $\Delta t$ may be a time interval such that the recorded temperature must remain within 1° C. of the desired calibration temperature before collecting a set of baseline data. Thus, the temperature interval $\Delta T$ and/or the dwell time $\Delta t$ may be selected dynamically based on continuous monitoring of the temperature. Alternatively, measurements may be made at arbitrary temperatures, and data sets may be repeatedly acquired until an adequate specified temperature range and value variations have been satisfied. A change profile decision block 380 will be discussed below.

If baseline data has previously been obtained at a given temperature (a Yes result in decision block 330), method 300 returns to block 320, and measurement is iterated until a different temperature is obtained. Temperature may be controlled from an external source, or temperature changes may occur through natural environmental (e.g., cyclic) processes. For example, a bridge or a building may undergo diurnal temperature cycles, so that $\Delta t$ may be on the order of hours. In another example, a satellite in full sunlight may have components with a rotation period of several minutes, so that $\Delta t$ may be on the order of several seconds to minutes. In addition, as a satellite revolves around the earth (e.g., in approximately 90 minutes) and spends approximately half that time in the earth's shadow, thermal load cycling may result in an additional Δt that may be on the order of several minutes. When a different temperature reading from among the selected temperature values is returned from the one or more temperature sensors (a No result in decision block 330), computer 240 proceeds to collect data (block 340) comprising signals transmitted along paths selected between pairs of transducers 215 of array 210 that provide a required degree of coverage for later detection of damage on structure 220.

The data corresponding to all selected actuator-sensor paths at a given temperature (or within a specified temperature range) is assembled into a data file and stored (block 350) in a baseline data space in machine readable memory 244 of computer 240. If the baseline data space is not completely filled, i.e., data is not yet acquired for all specified temperature values (a No result in decision block 360), method 300 returns to block 320 to make another temperature measurement until a new temperature, not previously obtained, is detected. If the baseline data space is completely filled, i.e., values have been obtained and data has been acquired (a Yes result in decision block 360) for all temperatures and paths, method 300 checks to see if the baseline data space is complete, and if a profile change of measurement conditions are desired. If no change in the measurement profile is required (a No in decision block 380), the method stops (block 370).

After completion of the temperature calibration method 300, the user may wish to modify the data sets for various reasons and acquire data under changed measurement conditions (a Yes result in profile decision block 380). For example, some data sets, which may correspond to data acquired at certain temperature readings, may no longer be valid, or may have noise or reading errors. Therefore, the user may wish to confirm the data (block 390), which may require repetition of a measurement under a certain environmental condition. Additionally, the user may decide, for example, to add additional increments of temperature, change the temperature range, or discard certain files, either because of data error, changes in the calibration profile, or other reasons. A Yes decision in block 380 forwards the method to a review process (block 390) to confirm and/or alter the calibration parameters, alter files (e.g., delete) and then returns operation of method 300 to continue the measurement loop at block 320.

Figure 4:
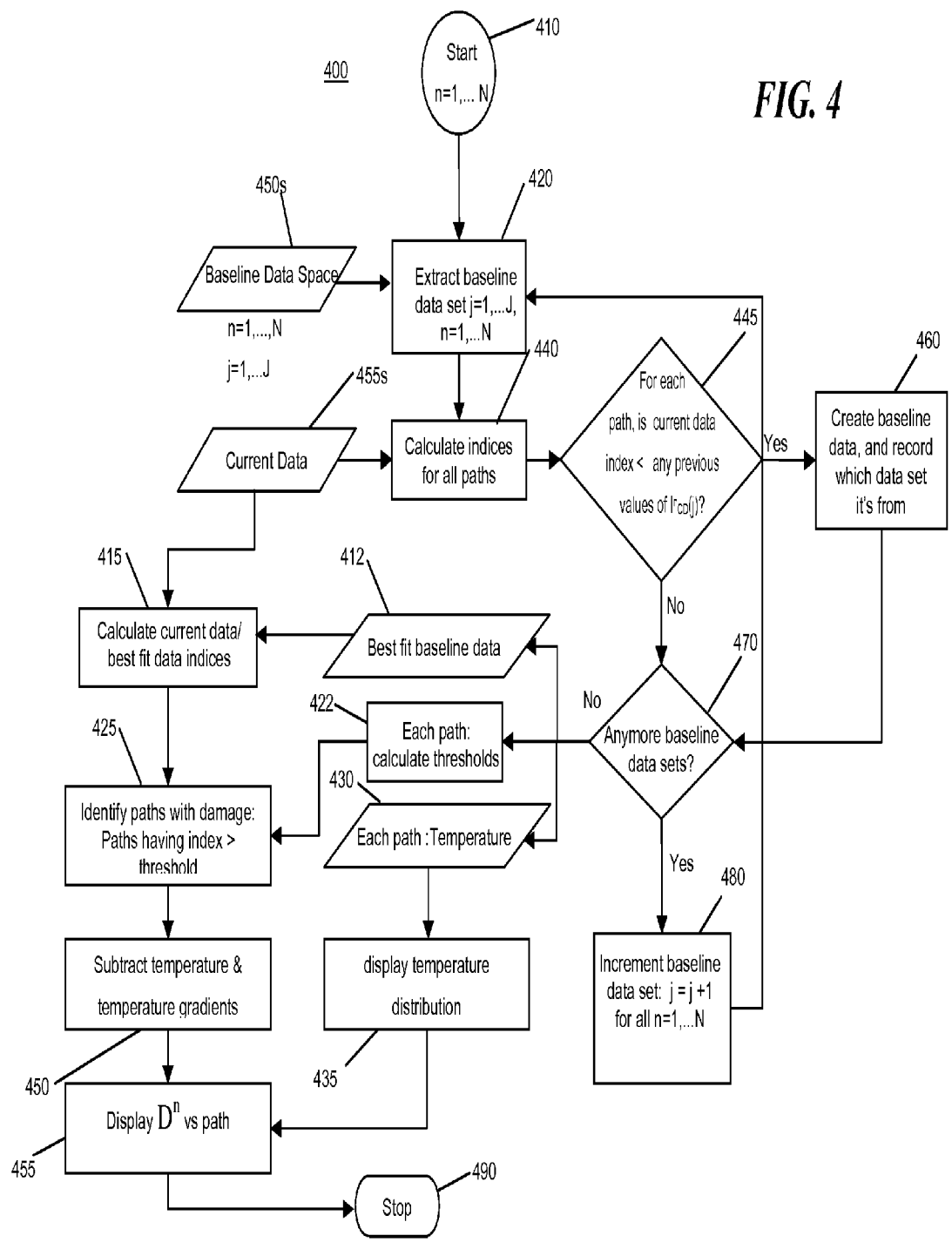
FIG. 4 is a flow chart of a process of compensating data for environmental change when detecting a signal according to an embodiment of the present disclosure.

When the baseline data space is completed, a compensated data signal detection method 400, shown in FIG. 4, may be implemented. Method 400 fits detected current signal data to the best fit with data obtained in calibration method 300. This best fit approach effectively yields the temperature of the structure along each path when temperature sensors may not be available or functional during actual health monitoring operational conditions. After a scan of structure 220 is performed—which may now potentially include damaged areas, the newly recorded signals (current data 455s) for each path are compared to the corresponding baseline space data sets 450s to determine a best fit for data at various temperatures. Temperature for the corresponding actuator-sensor path is determined according to this best fit, as indicated above, as well as identifying the baseline data set to be used for damage assessment. Method 400 may then detect changes due to damage relative to the best fit baseline data set. In the present embodiment, for simplicity of discussion, the structure may be assumed free of defects during temperature calibration and the baseline data space represents a reference for all subsequent measurements monitoring for damage detection within the specified temperature range.

Baseline data space 450s includes N paths (i.e., n=1, ... N) selected from array 210. In each selected path, a data signal corresponding to each of J selected values (i.e., j=1, ... J) of the environmental parameter (e.g., temperature) is included in baseline data space 450s. Referring to FIG. 4, method 400 starts (block 410) with a call to extract a first baseline signal data set (block 420) from baseline data space 450s (stored in block 350 of method 300) corresponding to the n=1th path, j=1st temperature value (or other environmental parameter value) which has been stored and maintained in machine readable memory 244. Using temperature as an example of an environmental parameter, start 410 assigns a counter j=1, ... J to the J baseline signal data sets in baseline space corresponding to the number of temperature values selected for a selected path n, and initializes j=1. For each selected path n of N paths, the data files in baseline data space 450s are selected one at a time according to the current value of j in block 420 and is compared with the current data set obtained for the same path n.

Current data 455s includes signal data sets corresponding to signals transmitted along the N selected path, which now may or may not contain a damage defect. Since baseline data space 450s is complete, current data 455s may now be acquired and temperature compensated detection of damage may proceed (described below).

For a given selected path n, one baseline signal data set (n,j) from baseline data space 450s may be chosen as a reference. For example, a reference baseline signal data set may be a signal acquired, for the selected path, at substantially the midpoint of the operational temperature range of the structural health monitoring system, although other reference points may be chose. All remaining baseline signal data sets may be compared to the reference baseline signal data set as follows: A single baseline signal data set for a selected path n comprises a waveform $X^n0$ that may be represented as a vector $X^n0(j)=\{X^n0_1(j), \ldots X^n0_m(j), \ldots X^n0_M(j)\}_j$, where j refers to the jth value of temperature (or other environmental effect variable value), and $X^n0_1(j), \ldots X^n0_m(j), \ldots X^n0_M(j)$ are M discrete values of a jth digitized record of the signal in the data set for the nth selected path. For simplicity, j=1 may be taken as identifying the reference temperature. All baseline signal data sets may be compared to the reference baseline data set by calculating a relative index—a baseline index $I_{BL}(j)$—for each baseline signal data set given, for example, by $$I^n_{BL}(j) = \frac{\sqrt{\sum_{m=1}^{M}(X0(j)_m - X0(1)_m)^2}}{\sqrt{\sum_{m=1}^{M}(X0(j)_m + X0(1)_m)^2}}, \quad (1)$$

where, for convenience, the superscript n in $X^n0(j)$ and X0n (1) have been left out of the equation but is implied. It is noted that when j=1, i.e., j identifies the reference baseline signal waveform, $I^n_{BL}(j)=0$, as expected, i.e., there is no difference between the baseline waveform being tested and the reference waveform. All baseline signal data waveforms acquired at temperatures increasingly distant from the reference temperature will result in a baseline index $I^n_{BL}(j)$ that increases correspondingly. FIG. 5 shows an exemplary graph of baseline index values $I_{BL}(j)$ for a given actuator-sensor path according to an embodiment of the present disclosure.

The properties of $I^n_{BL}(j)$ enable a threshold to be selected for each of the n paths on the basis of temperature (or other environmental effects) independent of details of the structure, signal levels in other paths, or other structure or system specific factors. For example, with reference to FIG. 5, the nearest neighbor value of $I^n_{BL}(j)$ may selected as a threshold value, the application of which will be described in more detail below. Alternatively, $2^{nd}$ or $3^{rd}$ nearest neighbor values may be selected instead. As will be seen, a smaller value of selected threshold implies more sensitivity in the detection of damage signals, whereas a larger selected threshold implies less sensitivity. Note that every one of the n paths may have a unique threshold regardless of the selected sensitivity parameter, since the indices of different selected path data sets are independently obtained.

Returning to FIG. 4, as described above, when baseline signal data set (n,j) is extracted (block 420) from baseline data space 450s, the relative baseline indices $I^n_{BL}(j)$ may be calculated (block 440) for all paths. Current data 455s may be acquired for each of the n paths, and current data indices $I^n_{CD}(j)$ relative to the j baseline signal data sets for path n may be computed, for example, in a fashion similar to that described above, given by:

$$I^n_{CD}(j) = \frac{\sqrt{\sum_{m=1}^{M}(X0(j)_m - X_{CD_m})^2}}{\sqrt{\sum_{m=1}^{M}(X0(j)_m + X_{CD_m})^2}}, \quad (2)$$

where, again, the path selection superscript n is assumed for $X^n0(j)$ and $X^n0_{CD}$, $X^n_{CD_m}$ is the mth value of M such digitized values in the current signal data waveform, which may be represented, by analogy with $X^n0(j)$, i.e., as a vector $X^n_{CD}$, and $I^n_{CD}(j)$ are the indices of the current signal data set computed relative to the baseline data set. One may note that when $X0(j)$ and $X_{CD}$ are identical, i.e., the waveforms have perfect overlap, then $I_{CD}(j)=0$, and an ideal match is found. Normally, however, this may not be the case, as various effects, such slight differences in the current and baseline temperature, signal noise, etc., in addition to damage, may result in differences in the measured current signal data waveform and any baseline waveform. However, seeking the minimum value of $I^n_{CD}(j')$ obtains a best fit of current data to the j'th baseline signal data set, and concurrently identifies the best fit corresponding j'th temperature. This is explained in detail below.

Once the index $I^n_{CD}(j)$ is calculated for the current data set (e.g., for the first temperature value, say j =1) for the path n (initially the n =1 path), a comparison must be made as to whether the current data index is less than or greater than any previously calculated current data index, i.e., $I^n_{CD}(j-1)$. Since j =1 is the first time the calculation is being made, $I^n_{CD}(j=0)$ may be set to an arbitrarily large value to insure that the first calculated current data index ($I^n_{CD}(1)$ becomes a first reference value. Since the first calculated index will be less than any previous value (a Yes result in decision block 445) the baseline data set used to calculate the current index is entered in a new baseline data set (block 460), and represents a best fit to the current data. For later calculated indexes that are not less than any previous value (a No result in decision block 445), the process skips block 460 and proceeds to block 470.

In decision block 470, an inquiry is made whether all J data sets for the path n have been obtained from baseline data space 450s to calculate more current data indices. If more baseline date sets remain to be compared to the current data set for the path n (a Yes result in decision block 470), j is incremented (block 480), and the next baseline dataset (j+1, n) is extracted (block 420) to repeat the index calculation (block 440) of current data versus the next baseline data set. When all J datasets for path n are exhausted, n is incremented to the next path. In the subsequent calculation the newly computed current data index may be less than any previously computed index (for the current path n)—a Yes result in decision block 445. In this case the current data set is a better fit to the j+1th baseline data set, and the j+1th baseline data set replaces the last baseline data set entered as the previous best fit.

In this loop, as described, block 460 creates a data base comprised of the single best fit baseline data sets corresponding to the current data sets 455s, which have been acquired by the health monitoring system for each of the N selected paths. When there are no more baseline data sets (i.e., all J data sets for all N paths have been examined for best fit)—a No result in decision block 470, method 400 proceeds to examine the relationship between the current data and the best fit baseline data to determine the temperature corresponding to the selected paths, compensate the data in terms of the best fit current data indices and identify the existence of damage in terms of the indices, as will now be described below.

The best fit baseline data selected in the previous steps (and accumulated in block 460) may be organized as follows: The resulting best fit baseline signal data may be stored in data block 412. For each selected path in block 422 the best fit baseline indices $I_{BL}(j)$ may be calculated and threshold values (whether nearest, next nearest, etc., neighbor values) of $I_{BL}(j)$ are chosen, for example, as describe in relation to equation (1). However, a threshold value of index may be chosen using other methods, including, for example, specifying an arbitrarily chosen numerical value for $I^n_{CD}$, which may be based on prior measurement experience. A data set 430 of temperatures corresponding to each of the best fit baseline signal data sets is formed corresponding to each path. Data blocks 412 and 430, and step 422 are provided for all selected paths in the structural health monitoring system. The temperature data set 430 may be displayed (block 435) as an array corresponding to the selected paths of the structure 220.

Under operational conditions of the structural health monitoring system, current data 455s may be acquired and compared to best fit baseline data 412 to calculate indices (in block 415) for best fit of the current data to the baseline data, $I_{CD}(j)$, using the prescription of eq. (2) and seeking the value j' for which $I_{CD}(j')$ is a minimum. In this manner, the "best fit" value j' of the environmental variable may be determined and used in subsequent damage detection. As distinguished from earlier calculations of $I_{BD}(j)$, where baseline data sets were being established, and a threshold value of the index is selected based on the change in index value for corresponding adjacent temperature values, now the possible existence of damage in the selected path of the structure may result in a set of indices $I_{CD}(j)$ for some paths that have a similar appearance as in FIG. 5, but are shifted upward, in recognition that new data differs from baseline data by the presence of damage.

In block 415 the current data set is compared to the best fit baseline data set (for the nth path) by examining the index value for the current data set relative to the best fit baseline data set. The current data indices obtained in block 415 are compared with the thresholds obtained in block 422 to identify paths with damage (in block 425) as follows: A difference $D^n = I^n_{CD}(j') - I^n_{BL}(j_{TH})$ is calculated for the selected path, where, again, $I^n_{CD}(j')$ is the best fit current data index, and $I^n_{BL}(j_{TH})$ is the index chosen from baseline data as the threshold, all for path n. If $D^n$ is positive, the best fit current data has an index that exceeds threshold and determines that there is damage in the path, and the level of damage may be indicated by assigning a value of, for example, $D''$ or $I''_{CD}(j')$. If $D''$ is equal to or less than zero, the best fit current data index does not exceed the threshold and determines that there is no damage detected. The absence of detected damage is indicated by assigning a value of zero.

By identifying damage in terms of the difference $D''$ of the current data index and the threshold, temperature and temperature gradient effects are automatically removed from the data (block 450), i.e., the data is compensated for environmental effects.

All assigned values of damage level (whether $D''$, $I_{CD}(j')$ or zero) may be assembled into an array corresponding to the N selected paths of structure 220 (block 455). The assembled array of damage level values provides a representation of damage data (in block 350) with temperature and temperature gradient effects removed from the data. The assembled array of damage level values may be displayed concurrently with, or separately from, the display of temperature data set 430 as provided in block 435. The process of FIG. 4 can then conclude (block 490).

A pulse that scatters or reflects from a defect that is not inline will proceed along an indirect path, thus having a longer time-of-flight, and arrive later in time. This signal can be blocked and rejected, for example, by time-gating or digital filtering. Alternatively, additional signal processing methods may be applied to the delayed reflection signals to obtain further structural health information.

An embodiment of threshold selection may be understood as follows: The threshold value is selected based only on baseline data. One temperature may serve as a reference. All other baseline signal data sets are at temperatures offset relative to the reference temperature. Thus, a baseline signal data set at a first adjacent increment of temperature from the reference will have an index greater than that calculated at the reference temperature, and baseline data corresponding to further increments from the reference temperature will have correspondingly greater index values. When collecting data during structural health monitoring, current data may be considered to show evidence of damage if the minimum index calculated for current data is greater than the threshold selected on the basis of baseline data, and the value of the index may be plotted, for example, as a color coded map, where the color coding corresponds to the excess value of the index of the current data over the threshold index. Current data that results in an index that is below the selected threshold may be ignored, e.g., not plotted. Selecting a higher threshold reduces the probability of specifying that a damage site has been detected. Selecting a lower threshold introduces more noise in the plot. The invention contemplates the selection of any threshold.

A threshold value using reflections from damage defects that are not directly on the selected path is contemplated by the invention, and may be determined in the same way as those for the first arrival of inline signals, except that the time windows may be different. Furthermore, one of ordinary skill in the art will realize that the invention encompasses the use of any suitable index, including those of equations (1)-(2), as well as others. In particular, the invention contemplates determination of any index that allows for selection of a damage detection threshold without independent detection of an environmental variable. Additionally, one of ordinary skill in the art will also realize that the methods and apparatuses of the invention can be employed to compensate for any environmental variable, and not just to compensate for temperature effects.

Having thus described embodiments of the present disclosure, persons of ordinary skill in the art will recognize that changes may be made in form and detail without departing from the scope of the invention. For example, whereas the embodiments previously described have been in the context of temperature change as the environmental change, other variables may be considered, such as humidity or moisture content in a graphite/epoxy structure, changing compressive or tensile load (either hydrostatic or tensor), strain, or pH. Other environmental factors may also be considered without limiting the invention, which is limited only by the following claims.

What is claimed is:

1. A method of compensating for environmental effect changes when detecting a signal, comprising:
    collecting baseline data signals at different values of an environmental effect variable, wherein the baseline data signals are propagated through a structure;
    for each of the values of the environmental effect variable, selecting a threshold based on the corresponding baseline data;
    collecting current data signals, wherein the current data signals are propagated through the structure;
    determining a value of the environmental effect variable corresponding to a closest match between the collected current data signals and the collected baseline data signals; and
    detecting damage in the structure by comparing collected current data signals to the threshold corresponding to the determined value of the environmental effect variable.

2. The method of claim 1, wherein the environmental effect variable is one or more of temperature, pressure, load, stress, strain, pH, moisture level, and humidity level.

3. The method of claim 1, wherein the collecting baseline data signals further comprises:
    selecting one or more paths between a plurality of transducers arranged in an array on a structure;
    selecting values of the environmental effect variable; and
    collecting data signals transmitted along the selected paths at the selected values of the environmental effect variable.

4. The method of claim 3, wherein the selecting a threshold further comprises:
    (A) selecting a value of the environmental effect variable;
    (B) selecting a path from the one or more paths;
    (C) comparing the baseline data signal corresponding to the selected value of the environmental effect variable to all remaining baseline data signals for all values of the environmental effect variable for the selected path;
    (D) computing a baseline index for each compared baseline data signal corresponding to the difference in compared baseline data signals to the remaining baseline data signals for the selected path; and
    (E) selecting a threshold value for the selected path from among the computed indices.

5. The method of claim 4, further comprising repeating (A), (B), (C), (D), and (E) for the remaining values of the environmental effect variable and the remaining ones of the one or more paths.

6. The method of claim 4, wherein the comparing the baseline data signal further comprises determining a difference between the baseline data signal corresponding to the selected value of the environmental effect variable for the selected path, and the remaining baseline data signals for the selected path.

7. The method of claim 4, wherein the computing a baseline index for each compared baseline data signal comprises calculating $$I_{BL}(j) = \frac{\sqrt{\sum_{m=1}^{M} (X0(j)_m - X0(1)_m)^2}}{\sqrt{\sum_{m=1}^{M} (X0_m(j) + X0(1)_m)^2}},$$

wherein $I_{BL}(j)$ is an index of the baseline data signal corresponding to the jth value of the environmental effect variable, $X0(j)$ is the jth baseline data signal corresponding to a jth value of the environmental effect variable, $X0(1)$ is the baseline data signal corresponding to a first value of the environmental effect variable, and m identifies the mth value of $X0(j)$ and $X0(1)$ in the M elements of the respective data signals.

8. The method of claim 4, wherein the selecting a threshold value comprises selecting an index $I_{BL}(j_{TH})$ as the threshold value, where $j=j_{TH}$ is a threshold value of the environmental effect variable, and where the threshold value is a value other than $I_{BL}(0)$.

9. The method of claim 8, wherein the collecting data signals comprises:
   selecting one or more paths between a plurality of transducers arranged in an array on a structure;
   collecting a current data signal transmitted on a first selected path between two transducers; and
   repeating the collecting a current data signal for all selected paths.

10. The method of claim 9, wherein the determining a value further comprises:
   computing an index for the current data corresponding to each of the baseline signal data sets for the selected path, wherein the computing comprises calculating $$I_{CD}(j) = \frac{\sqrt{\sum_{m=1}^{M} (X0(j)_m - X_{CD_m})^2}}{\sqrt{\sum_{m=1}^{M} (X0(j)_m + X_{CD_m})^2}},$$

wherein $I_{CD}(j)$ is an index of the current data signal relative to the jth baseline data signal at the jth value of the environmental effect variable, $X_{CD}$ is the current data signal, and m identifies the mth data point value of $X0(j)$ and $X_{CD}$ in the M elements of the respective data signals; and
   selecting a baseline data signal $X0(j')$ for which $I_{CD}(j')$ is a minimum of all computed values of $I_{CD}(j)$ as the best match to the current data signal for the selected path.

11. The method of claim 10, wherein the determining a value further comprises selecting the value of the environmental effect variable corresponding to $X0(j')$.

12. The method of claim 11, wherein the detecting damage further comprises:
   determining a difference $D=I_{CD}(j')-I_{BL}(j_{TH})$;
   determining that damage is detected if D is greater than zero; and
   determining that no damage is detected if D is equal to or less than zero.

13. A system for compensating for environmental effect changes in data in a structural health monitoring system operably coupled to a structure, the system comprising:
   one or more transducers configured in an array attached to the structure;
   a first software module storing instructions for acquiring and processing data from the array to provide a baseline data set for compensating for values of an environmental effect variable, and selecting damage detection thresholds each corresponding to one of the values of the environmental effect variable;
   a second software module storing instructions for processing current signal data acquired from the array to detect damage in the structure by determining from the current signal data a corresponding value of the environmental effect variable, and comparing the current signal data to the damage detection threshold associated with the corresponding value of the environmental effect variable;
   a memory storing the first and second software modules;
   a processor to execute instructions of the first and second software modules; and
   a display operably coupled to the processor for presentation of the damage.

14. The system of claim 13, wherein the transducers are at least one of piezoelectric, magneto-elastic, and electrostatic transducers adapted to excite elastic waves in the structure.

15. The system of claim 13, wherein the environmental effect variable is one or more of temperature, pressure, load, stress, strain, pH, moisture level, and humidity level.

16. The system of claim 13, wherein the first and second software modules are the same software module.

17. The system of claim 13, wherein the software module for collecting baseline data signals is adapted to:
   select one or more paths between a plurality of transducers arranged in an array on a structure;
   select values of the environmental effect variable; and
   collect data signals transmitted along the selected paths at the selected values of the environmental effect variable.

18. The system of claim 13, wherein the software module for selecting a threshold is adapted to:
   (A) select a value of the environmental effect variable;
   (B) select a path from the one or more paths;
   (C) compare the baseline data signal corresponding to the selected value of the environmental effect variable to all remaining baseline data signals for all values of the environmental effect variable for the selected path;
   (D) compute a baseline index for each compared baseline data signal corresponding to the difference in compared baseline data signals to the remaining baseline data signals for the selected path; and
   (E) select a threshold value for the selected path from among the computed indices.

19. The system of claim 18, wherein the software module for selecting one or more damage detection thresholds is adapted to:
   repeat (A), (B), (C), (D), and (E) for the remaining values of the environmental effect variable and the remaining ones of the one or more paths.

20. The system of claim 18, wherein the software module for selecting one or more damage detection thresholds is adapted to:
   determine a difference between the baseline data signal corresponding to the selected value of the environmental effect variable for the selected path, and the remaining baseline data signals for the selected path.

* * * * *

UNITED STATES PATENT AND TRADEMARK OFFICE
CERTIFICATE OF CORRECTION

| | |
|---|---|
| PATENT NO. | : 7,809,513 B2 |
| APPLICATION NO. | : 11/952936 |
| DATED | : October 5, 2010 |
| INVENTOR(S) | : Shawn J. Beard, Bao Liu and Fu-Kuo Chang |

It is certified that error appears in the above-identified patent and that said Letters Patent is hereby corrected as shown below:

Col. 1, after "BRIEF DESCRIPTION OF THE INVENTION" please insert the following paragraph:

--GOVERNMENT LICENSE RIGHTS
 This invention was made with Government support under contract number FA8650-05-C3509 awarded by the U.S. Air Force. The Government has certain rights in the invention.--

Signed and Sealed this
Sixteenth Day of October, 2012

David J. Kappos
*Director of the United States Patent and Trademark Office*